(12) United States Patent
Forster et al.

(10) Patent No.: US 11,953,669 B2
(45) Date of Patent: Apr. 9, 2024

(54) OPTICAL OBSERVATION INSTRUMENT AND METHOD FOR CREATING A STEREO IMAGE OF AN OBJECT FIELD

(71) Applicant: KARL STORZ SE & Co. KG, Tuttlingen (DE)

(72) Inventors: Jonas Forster, Tuttlingen (DE); Sebastian Barth, Tuttlingen (DE); Andreas Heni, Tuttlingen (DE); Benedikt Köhler, Tuttlingen (DE); Walter Vogel, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 366 days.

(21) Appl. No.: 17/145,495

(22) Filed: Jan. 11, 2021

(65) Prior Publication Data
US 2021/0215922 A1    Jul. 15, 2021

(30) Foreign Application Priority Data
Jan. 14, 2020    (DE) .................... 10 2020 100 674.8

(51) Int. Cl.
G02B 21/36    (2006.01)
A61B 90/00    (2016.01)
(Continued)

(52) U.S. Cl.
CPC ............ G02B 21/361 (2013.01); A61B 90/20 (2016.02); A61B 90/361 (2016.02);
(Continued)

(58) Field of Classification Search
CPC ............. G02B 21/361; G02B 21/0012; G02B 21/368; G02B 21/362; G02B 21/365;
(Continued)

(56) References Cited

U.S. PATENT DOCUMENTS 4,168,904 A    9/1979    Furukawa
5,162,647 A    11/1992    Field, Jr.
(Continued)

FOREIGN PATENT DOCUMENTS

CN    106200213 B    1/2019
DE    10130119 A1    1/2002
(Continued)

OTHER PUBLICATIONS

U.S. Appl. No. 17/145,470, filed Jan. 11, 2021, Forster.
(Continued)

*Primary Examiner* — Derek S. Chapel
*Assistant Examiner* — Adam W Booher
(74) *Attorney, Agent, or Firm* — Jason H. Vick; Sheridan Ross, PC

(57) ABSTRACT

An optical observation instrument according to the invention, in particular a surgical microscope or exoscope, comprises an optics unit with an objective arrangement and at least one electronic image recorder, wherein the optics unit has a first stereo channel with a first beam path and a second stereo channel with a second beam path for recording a stereo image of an object field with the at least one electronic image recorder and wherein the first and the second beam path extend through the objective arrangement. The instrument moreover comprises a retaining apparatus, on which the optics unit is mounted so as to be rotatable about a first axis of rotation, the latter at least approximately corresponding to an axis of the objective arrangement, wherein the optical observation instrument has a viewing direction that is angled in relation to the axis of the objective arrangement and comprises a deflection element, arranged on the object-side of the objective arrangement, for deflecting the first and the second beam path into the objective arrangement. The
(Continued)

invention further relates to a method for generating a stereo image of an object field.

20 Claims, 6 Drawing Sheets

(51) Int. Cl.
 *A61B 90/20* (2016.01)
 *G02B 21/00* (2006.01)
 *G02B 27/64* (2006.01)
(52) U.S. Cl.
 CPC ....... *G02B 21/0012* (2013.01); *G02B 27/642* (2013.01); *G02B 21/368* (2013.01)
(58) Field of Classification Search
 CPC ...... G02B 21/367; G02B 21/36; G02B 21/18; G02B 21/20; G02B 21/22; G02B 21/04; G02B 27/642; A61B 90/20; A61B 90/361; A61B 2090/3618; A61B 90/25
 See application file for complete search history.

(56) References Cited

U.S. PATENT DOCUMENTS

| | | | |
|---|---|---|---|
| 5,852,519 | A | 12/1998 | Do et al. |
| 7,133,198 | B2 | 11/2006 | Schnitzler et al. |
| 10,571,309 | B2 | 2/2020 | Grau |
| 2001/0055150 | A1 | 12/2001 | Ito |
| 2004/0017607 | A1 | 1/2004 | Hauger et al. |
| 2005/0111090 | A1 | 5/2005 | Kleinteich et al. |
| 2006/0132779 | A1 | 6/2006 | Hunt et al. |
| 2010/0110538 | A1 | 5/2010 | Steffen et al. |
| 2011/0134518 | A1* | 6/2011 | Doi ........................ A61B 90/20 359/384 |
| 2011/0299174 | A1 | 12/2011 | Obrebski |
| 2012/0243079 | A1 | 9/2012 | Böhm et al. |
| 2012/0265023 | A1 | 10/2012 | Berci et al. |
| 2013/0140411 | A1* | 6/2013 | Frick ........................ F16M 11/00 248/125.1 |
| 2014/0347461 | A1 | 11/2014 | Kleppe |
| 2015/0085084 | A1 | 3/2015 | Heni et al. |
| 2016/0286197 | A1 | 9/2016 | Schwarz et al. |
| 2017/0146780 | A1 | 5/2017 | Nakamura |
| 2018/0164568 | A1* | 6/2018 | Kubek ..................... G02B 7/16 |
| 2019/0079248 | A1 | 3/2019 | Hagen et al. |

FOREIGN PATENT DOCUMENTS

| | | |
|---|---|---|
| DE | 10336890 A1 | 3/2005 |
| DE | 102006004232 A1 | 8/2007 |
| DE | 102009011681 A | 8/2010 |
| DE | 102009019575 A1 | 11/2010 |
| DE | 202011000688 U1 | 6/2011 |
| DE | 102011054031 A1 | 10/2012 |
| DE | 102013110543 A1 | 3/2015 |
| EP | 1333305 B1 | 8/2003 |
| EP | 1538471 A1 | 6/2005 |
| EP | 1333305 B1 | 4/2007 |
| EP | 2514357 A1 | 10/2012 |
| EP | 3073307 A1 | 9/2016 |
| EP | 3178434 A1 | 6/2017 |
| EP | 3197146 A1 | 7/2017 |
| EP | 3514595 A1 | 7/2019 |
| WO | WO-2015016166 A1 * | 2/2015 ......... A61B 1/00193 |
| WO | WO 2019/120553 A1 | 6/2019 |
| WO | WO 2019/181149 A1 | 9/2019 |

OTHER PUBLICATIONS

Image of an Arriscope Instrument—Date Unknown.
Screenshot of an Image of an Arriscope Instrument—Date Unknown.
Office Action for corresponding German Application No. 102020100676.4, dated Aug. 31, 2020.
Office Action for corresponding German Patent Application No. 102020100674.8, dated Aug. 28, 2020.
Extended European Search Report for corresponding European Application No. 21150897.3, dated Jun. 22, 2021.
Extended European Search Report for corresponding European Application No. 21150921.1, dated Jun. 10, 2021.
Office Action for U.S. Appl. No. 17/145,470, dated Feb. 8, 2023.
Notice of Allowance for U.S. Appl. No. 17/145,470, dated Jul. 19, 2023.

* cited by examiner

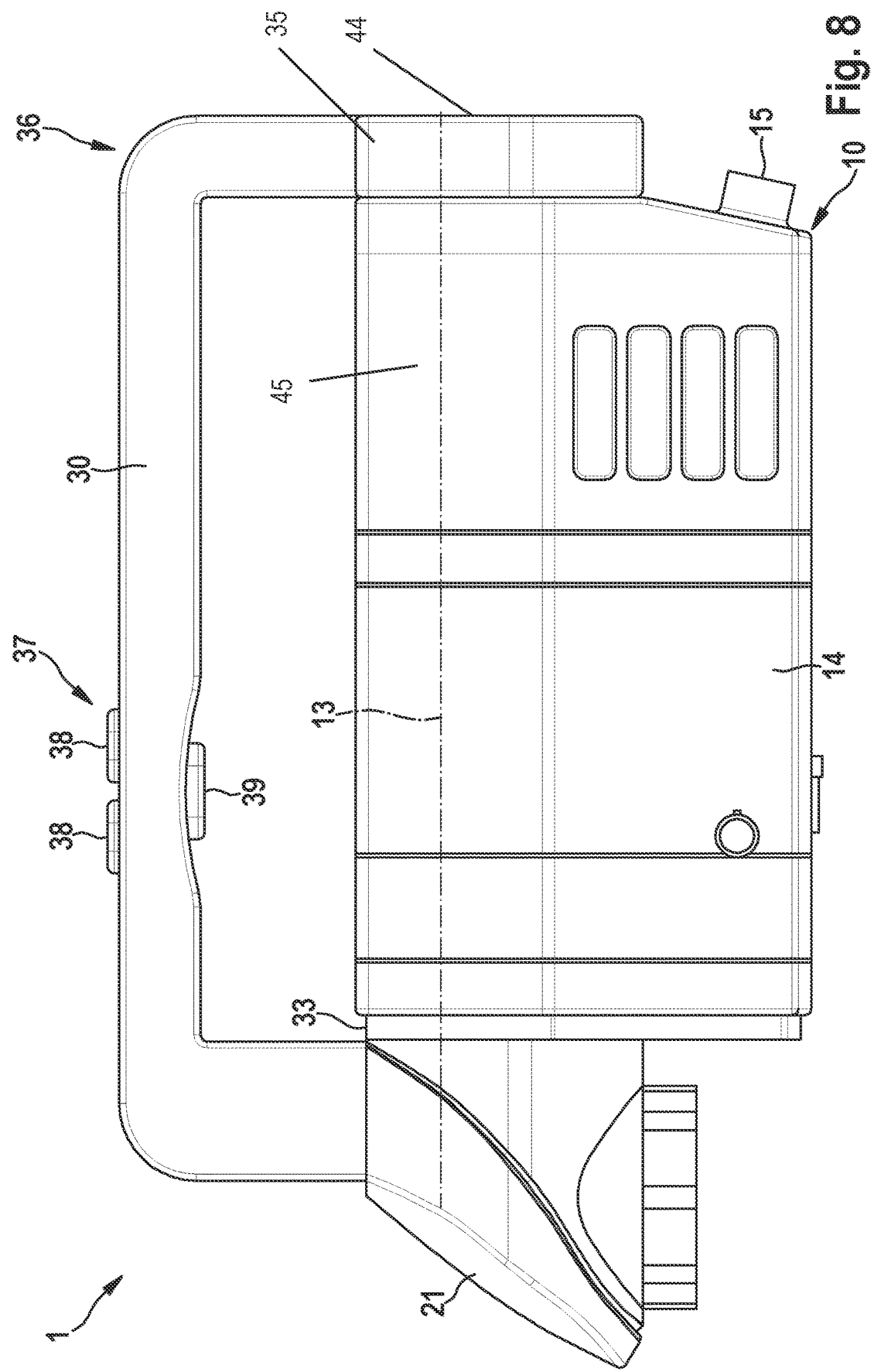

OPTICAL OBSERVATION INSTRUMENT AND METHOD FOR CREATING A STEREO IMAGE OF AN OBJECT FIELD

CROSS-REFERENCE TO RELATED APPLICATIONS

This application claims the benefit under 35 U.S.C. 119(a) to German Patent Application No. 10 2020 100 674.8, filed Jan. 14, 2020, the disclosure of which is incorporated herein by reference in its entirety

SUMMARY

The present invention relates to an optical observation instrument, in particular a surgical microscope or an exoscope, in accordance with the preamble of claim 1, and to a method for generating a stereo image of an object field.

To observe an operating field during a surgical intervention on a human or animal body, optical observation instruments have been disclosed, which provide a surgeon and, possibly, further persons with an accurate or magnified observation of the operating field on the body with, at the same time, the access to the operating field not being substantially restricted. Such optical observation instruments can be embodied, in particular, as a surgical microscope or as an exoscope.

DE 10 2011 054 031 A1 has disclosed an apparatus for observing and illuminating an object field on a patient from a location away from the body of the patient, said apparatus comprising optics for observing the object field and an illumination for illuminating the object field. Further, the apparatus comprises a shaft, at the distal end of which a head part is arranged, which is expanded in relation to the shaft and in which an illumination unit for illuminating the object field is arranged. The elongate shaft can receive an image transfer means, which transfers the image of the operating field to a proximal end of the shaft. Such an apparatus is also referred to as an "exoscope". This facilitates the illumination and observation of an operating field during a surgical operation from a working distance of 25 to 75 cm, for example, and so the workspace of the surgeon is practically not restricted by the exoscope. Connecting a video camera allows the image of the object field to be displayed on a screen, and so the surgeon and possibly further persons are able to observe said image without tiring. The exoscope can be retained by an adjustable retainer.

A spatial perception of the object field is helpful to the operating surgeon when carrying out a surgical operation. Facilitating an improved spatial perception of the object field by way of stereoscopic optics, in which two images of the object field are recorded from slightly different perspectives, is known. The two images which, together, represent the stereoscopic image are also referred to as "half images" or as "stereo half images". The two half images are separately presented to the right and the left eye of the surgeon, and so the latter can obtain a spatial impression of the object field. For example, a monitor suitable for a stereoscopic display can be provided for this, for instance a screen with alternating polarization, with the surgeon wearing polarization glasses with different polarizations of the two lenses.

However, the problem arising when using stereoscopic optics is that a rotation about an axis parallel to the viewing direction of the optics rotates not only the image generated using electronic image recorders, and hence also the image of the operating field displayed on a screen, but also, moreover, the baseline of the stereoscopic optics. The same applies if the surgeon changes their own position. Both cases make it more difficult, or even impossible, for the surgeon to orient themselves in the operating field. An electronic image erection is not possible, in turn, since a rotation of the two half images of the stereo image would not lead to rotation of the stereo basis, i.e., the imagined line between the two centers of the apertures of the stereo optics. Therefore, the stereo impression would be lost. It is therefore necessary to be able to accordingly adapt the stereo basis of the stereoscopic optics in order to facilitate an image erection or an alignment of the horizon.

According to DE 10 2013 110 543 A1, an exoscope comprises a shaft and observation optics which are arranged at a distal end of the shaft and which serve to record the image of the object field, wherein the observation optics are embodied as stereo optics with at least one electronic image recorder for recording a stereo image of the object field. The exoscope comprises an optics unit which is arranged in a head part arranged at the distal end of the shaft and which comprises the observation optics. The optics unit is rotatable about an axis of rotation approximately parallel to a viewing direction of the observation optics, wherein the viewing direction may be angled by approximately 90° with respect to the longitudinal axis of the shaft. During a surgical operation and for the purposes of observing a horizontally arranged object field, for instance an operating field during a surgical operation on the human body, the exoscope can, as a result, be positioned over the object field with a viewing direction directed in perpendicular downward fashion. In the process, a stereoscopic image of the object field can be recorded and an erection of the recorded and displayed image of the object field and an adjustment of the stereo basis can be undertaken when swiveling the exoscope.

EP 1 333 305 B1 proposes a stereo examination system for imaging an object, which comprises an objective arrangement with an optical axis and an object plane, wherein the objective arrangement receives an object-side beam emitted from the object plane within a solid angle region and converts said beam into an image-side beam. Further, the stereo examination system comprises a selector arrangement for selecting a first and a second pair of partial beams from the image-side beam and an image transfer apparatus for generating representations of the images of the object provided by the first and second pair of partial beams. The selector arrangement is embodied to displace a beam cross section of at least one of the partial beams relative to a beam cross section of the image-side beam, wherein a controller is provided in order to drive the selector arrangement to displace the beam cross section of the at least one partial beam in the circumferential direction about the optical axis.

For the observation of the recorded image by the surgeon, it was found to be advantageous to arrange one or more screens (monitors) in an elevated position relative to the position of the surgeon such that the surgeon can gaze at the image displayed on the monitor above the operating field, above possibly used surgical instruments and above the optical observation instrument. However, as a rule, surgical microscopes, in particular, have an elongate and large microscope body, which prevents an unimpeded view over the optical observation instrument or which would require a disadvantageously high position of the monitor that is considered uncomfortable by the observer. In exoscopes, too, the head part can restrict the visual field of the surgeon, with the installation height of the head part being determined by the length of the optics unit, in particular.

It is an object of the present invention to specify an optical observation instrument, in particular a surgical microscope or an exoscope with stereo optics, which does not have the aforementioned disadvantages, wherein a vertical installation height of the optical observation instrument is reduced, particularly in the case of a vertically downwardly directed viewing direction. Further, it is an object of the invention to specify an improved method for generating a stereo image of an object field.

This object is achieved by an optical observation instrument as disclosed herein.

Advantageous developments of the invention emerge from the dependent claims.

An optical observation instrument according to the invention is, in particular, a medical optical observation instrument and is, preferably, embodied as a surgical microscope or as an exoscope. By way of example, the optical observation instrument can serve to record an image of an object field on a human or animal body from outside of the body. By way of example, the object field can be an operating field of a surgical intervention. Here, the observation instrument is preferably embodied to record the image of the operating field from a working distance which provides a surgeon with an unimpeded access to the operating field during the surgical intervention. By way of example, the working distance can be in the range of approximately 10 to 75 cm, preferably approximately 15 to 50 cm. When reference is made to a "user" of the optical observation instrument below, this refers, in particular, to an operating surgeon or surgeon; however, a user can also be a person, for example, who assists the surgeon during the intervention or a further observer of the intervention, or else a user in the case of non-medical applications of the optical observation instrument.

The optical observation instrument according to the invention comprises an optics unit, which comprises an objective arrangement and at least one electronic image recorder. The optics unit is embodied to record a stereo image of an object field, for example an object field on a human or animal body, with the at least one electronic image recorder and consequently embodied as stereo optics. To this end, the optics unit has a first stereo channel with a first beam path and a second stereo channel with a second beam path, for recording a first and a second stereo half image of the object field. Here, provision can be made for the object field to be imaged by means of the objective arrangement on a first electronic image recorder via the first beam path in order to record the first stereo half image and for the object field to be imaged by means of the objective arrangement on a second electronic image recorder via the second beam path in order to record the second stereo half image of the object field. Instead of a first and a second electronic image recorder, a single image recorder, for example, can also serve to record the first and the second stereo half image, wherein the first and the second stereo half image of the object field are imaged on different regions of the image recorder. In particular, the at least one electronic image recorder is a CCD or MOSFET image sensor.

The first and the second beam path extend through the objective arrangement. The objective arrangement serves, in particular, to image the object field on the first and the second image recorder or on corresponding regions of a single image recorder via the first and the second beam path, respectively. The objective arrangement can comprise common imaging optical elements, which are common to the first and second stereo channel and, optionally, further imaging optical elements which are respectively assigned to the first or the second stereo channel only, for instance one or more front lenses or one or more zoom optics. However, the objective arrangement can also comprise an objective of the first stereo channel and an objective of the second stereo channel, which can be embodied separately from one another. The objective arrangement can be embodied as an assembly and can consequently form an objective unit of the optics unit. In particular, the objective arrangement is embodied as a lens system, although it can also comprise reflecting optical elements. Further, the objective arrangement can comprise one or more filters which are assigned to the first and the second stereo channel together or which are respectively assigned to the first or the second stereo channel only, for example one or more fluorescence filters. In particular, the filters can be set up to observe and record fluorescence light and to filter the excitation light of the fluorescence. Hence, the observation instrument can be embodied, in particular, for a simultaneous observation of fluorescence by the dyes ICG (indocyanine green), fluorescein and PPIX (protoporphyrin IX).

The objective arrangement has an axis, which can be, for example, an optical axis of an objective lens or of a lens system, which objective lens or lens system is passed by the first and the second beam path. In the case where the first and the second stereo channel each comprise a separate objective, the axis is, in particular, a center axis of the two beam paths or of the optical axes of the two objectives. The first and the second beam path are offset from one another transversely to the axis of the objective arrangement, wherein a stereo basis of the stereo optics is determined by the connecting line between the first and the second beam path, in particular in an object-side element of the objective arrangement. The first and the second beam path can extend at an angle to one another on the object side of the objective arrangement, with the inclusion of a stereo angle such that the beam paths intersect or at least overlap at a preferred working distance, for example at a distance of approximately 25 cm. However, the first and the second beam path can also extend parallel to one another on the object side of the objective arrangement; the working distance, and hence the stereo angle, then emerge, in particular, by the focus set and/or by a disparity of the recorded stereo half images, or vice versa. In particular, the axis of the objective arrangement can be an angle bisector between the object-side sections of the first and the second beam path.

Further, the optical observation instrument comprises a retaining apparatus, which preferably has an adjustable embodiment, wherein the optics unit is mounted on the retaining apparatus in a manner rotatable about a first axis of rotation. The first axis of rotation corresponds at least approximately to the axis of the objective arrangement, the latter possibly being, for example, the optical axis of a common objective lens and/or a center axis between the optical axes of the first and the second stereo channel. The retaining apparatus can be embodied in such a way that it is possible to fasten the latter to an operating table. What this can achieve is that the optics unit is rotatable relative to the operating table about the optical axis. The rotatable mount can facilitate a rotation of the stereo basis, and so the stereo basis can be set in accordance with the location of a user and the alignment of the optical observation instrument in order to provide the user with a natural stereo impression in the case of an erected image or an image aligned with the horizon and with simple orientation within the object field. Thus, a rotation of the optics unit preferably corresponds to a rotation of the stereo basis about an axis perpendicular to the stereo basis.

According to the invention, the optical observation instrument has a viewing direction that is angled in relation to the axis of the objective arrangement and comprises a deflection element which is arranged on the object side of the objective arrangement and which is embodied and arranged to deflect the first and the second beam path into the objective arrangement. The optical deflection element can comprise one or more reflecting surfaces. Here, the viewing direction is, in particular, a mean direction between the viewing directions of the first and the second stereo channel or the object-side sections of the first and the second beam path. Consequently, the optical deflection element is arranged and embodied to deflect the first and the second beam path from their respective viewing directions into the objective arrangement and hence into the optical elements of the first and the second stereo channel for generating the first and the second stereo half image, wherein the mean direction between the viewing directions of the first and the second beam path corresponds to the viewing direction of the observation instrument, which is angled in relation to the axis of the objective arrangement. Accordingly, in particular a central axis or an angle bisector between the object-side sections of the first and the second beam path which meet at the preferred working distance can be considered to be a viewing axis of the optical observation instrument, the direction of which corresponds to the viewing direction. The object-side sections of the first and the second beam path or their respective viewing directions then respectively form an angle with the viewing axis, which corresponds to half the stereo angle. In the case where the object-side sections of the first and the second beam path extend parallel to one another, the viewing direction of the optical observation instrument corresponds to the viewing directions of the first and the second beam path and the viewing axis is, in particular, a central axis between the object-side sections of the first and the second beam path, which is angled in relation to the axis of the objective arrangement.

In particular, this means that an object-side beam path of the optical observation instrument is deflected into the objective arrangement at least approximately in the direction of the axis of the objective arrangement by the optical deflection element from a viewing direction that is angled in relation to the axis of the objective arrangement. The object-side beam path can be formed by beams emanating from the object field that are emitted into a conical solid angle range surrounding the viewing axis, which beams are deflected by the deflection element toward the objective arrangement, wherein those of these beams that form the first and the second beam path and enter into the optical elements of the first and the second stereo channel are imaged on the at least one electronic image recorder for the purposes of generating the first and the second stereo half image. Here, the viewing axis is the axis of the conical solid angle range, which has an aperture angle approximately corresponding to the stereo angle. In particular, the beams coming from the object field, which beams are deflected by the deflection element, are incident on the objective arrangement in an appropriate solid angle range surrounding the axis of the objective arrangement so that respective components of the incident light reach the first and the second stereo channel and are imaged on the relevant image recorders or regions of the image recorder.

As a result of the optical observation instrument, which is a stereo surgical microscope or a stereo exoscope in particular, having a viewing direction that is angled to the axis of the objective arrangement, particularly advantageous handling can be facilitated. What can be achieved thereby, in particular, is that an installation length of the optics unit in the direction of the axis of the objective arrangement does not extend in the viewing direction, wherein the installation length of the optics unit can be determined, inter alia, by a length of the first and the second beam path and can consequently be specified by the optical requirements placed on the optical observation instrument. Consequently, if the viewing direction of the optical observation instrument is directed vertically downward at an operating field on a human or animal body, the vertical installation height of the optical observation instrument, for example the installation height of a head part of a stereo exoscope, is not specified by the installation length of the optics unit but can be chosen to be smaller. This can reduce or avoid restriction of the visual field of a surgeon when gazing at a monitor arranged on the opposite side.

Further, a viewing direction of the optical observation instrument that is angled relative to the axis of the objective arrangement can easily be realized as a result of an optical deflection element being arranged on the distal side of the objective. As a result of the optics unit, and hence the stereo basis defined by the arrangement of the first and the second stereo channel of the optics unit, being able to be rotated at least approximately about the axis of the objective arrangement or the center axis of the beam paths, it is possible in a particularly simple and advantageous manner in this case to facilitate an adaptation of the direction of the stereo basis to a location of the user and the alignment of the observation instrument, and an erection of the stereo image. By way of example, in the case where the viewing direction of the optical observation instrument is directed at an operating field or a body region of a patient lying on an operating table, it is possible to easily set the stereo basis for different locations of the user in such a way that the stereo image yields a natural spatial and erected impression of the operating field or of the observed region of the body surface. Consequently, this can allow the surgeon to freely position the optics unit and subsequently be able to set the stereo basis in accordance with their location and the natural or preferred horizon, wherein a significant restriction of their visual field can be avoided at the same time.

In particular, the optics unit is mounted here in a manner rotatable relative to the retaining apparatus and relative to the deflection element.

Preferably, the viewing direction is angled at least approximately at 90° in relation to the axis of the objective arrangement. What this can facilitate is that the optics unit extends in approximately horizontal direction and is rotatable about an approximately horizontal axis in order to set the direction of the stereo basis in the case of a viewing direction directed approximately vertically downward, this being a particularly advantageous viewing direction for a surgical intervention as a rule. What this can achieve is that, firstly, the object field is freely accessible, in particular that an operating field is freely accessible to the surgeon, and, secondly, a largely unimpeded view over the optical observation instrument on a monitor is possible, said monitor possibly being arranged, for example, opposite the surgeon next to the operating table.

In a particularly preferred manner, the optics unit comprises a housing with an elongate embodiment or a stretched-out housing, which is referred to as optics housing below and which extends at least approximately in the direction of the axis of the objective arrangement. Here, optical elements of the optics unit in particular, in particular the objective arrangement, preferably all optical elements or all lenses of the optics unit, are received within the optics housing. An elongate or stretched-out embodiment of the optics unit facilitates a particularly advantageous configuration of the first and the second beam path for generating the two stereo half images. According to this embodiment, a longitudinal direction of the optics housing is consequently at least approximately parallel to the axis of the objective arrangement and the first axis of rotation, in respect of which the optics unit is mounted on the retaining apparatus in rotatable fashion, is at least approximately parallel to the longitudinal direction of the optics housing. Therefore, the optical observation instrument can be retained, for example, above an operating table in such a way that the viewing direction is approximately directed downwardly in the vertical direction and a longitudinal direction of the optics unit or of the optics housing, which is approximately parallel to the axis of the objective arrangement and the first axis of rotation, is directed horizontally. Firstly, this develops a particularly advantageous structure of the optics unit and, secondly, this allows a user to view a monitor over the optical observation instrument without a substantial restriction of the working region and the visual field. By way of example, the optics housing can represent a microscope body of a surgical microscope.

According to a particularly preferred embodiment of the invention, the optics housing of the optics unit is mounted so as to be rotatable relative to the retaining apparatus about the first axis of rotation and contains optical elements of the optics unit, in particular the objective arrangement, preferably all optical elements or all lenses of the optics unit, and the at least one electronic image recorder, for example at least two electronic image recorders, for recording the first and the second stereo half image, wherein the viewing direction of the optical observation instrument further is angled by approximately 90° in relation to the first axis of rotation, as described above.

According to a preferred embodiment of the invention, the objective arrangement comprises an object-side front lens, wherein the first and the second beam path extend through the front lens. In this case, the axis of the objective arrangement is, in particular, an optical axis or a center axis of the front lens, which can preferably simultaneously be a center axis between the first and the second beam path or between optical axes of the first and the second beam path. In particular, the first and the second beam path or the optical axes thereof extend through the front lens in symmetrical fashion with respect to the axis of the objective arrangement, wherein the object-side sections of the first and the second beam path can extend parallel or at an angle to one another and approximately include the stereo angle, and the sections of the first and the second beam path adjoining the front lens on the image side can extend parallel to one another and to the axis of the objective arrangement. According to this embodiment of the invention, the optical observation instrument consequently comprises an optics unit with an objective arrangement, which comprises an object-side front lens, and at least one electronic image recorder, wherein the optics unit has a first stereo channel with a first beam path and a second stereo channel with a second beam path for recording a stereo image of an object field using the at least one electronic image recorder and wherein the first and the second beam path extend through the front lens, and a retaining apparatus, on which the optics unit is mounted so as to be rotatable about a first axis of rotation, said first axis of rotation at least approximately corresponding to the optical axis of the front lens, wherein the optical observation instrument comprises a deflection element, arranged on the object side of the front lens, for deflecting the first and the second beam path from their respective viewing directions into the objective arrangement, wherein a mean direction of the viewing directions, which is the viewing direction of the observation instrument, is angled with respect to the optical axis of the front lens. This can facilitate a particularly simple configuration with a large rotation angle range of the optics unit.

In a particularly preferred manner, the optical deflection element comprises a plane mirror, preferably exactly one plane mirror, standing obliquely to the axis of the objective arrangement. In particular, the deflection element can be embodied as such a plane mirror. In the case where the viewing direction of the optical observation instrument is angled by approximately 90° with respect to the axis of the objective arrangement, the surface normal of the plane mirror is approximately at an angle of 45° to the axis of the objective arrangement. The plane mirror preferably has only a single reflecting surface in order to prevent double reflections from arising. As a result of the deflection element being embodied as a mirror arranged at an angle to the axis of the objective arrangement, for example at an angle to the optical axis of the front lens, it is possible to facilitate a particularly light and simple construction. Alternatively, the deflection element could be embodied as a prism or prism arrangement.

Preferably the optical deflection element is arranged on the retaining apparatus. By way of example, the optical deflection element can be arranged in fixed fashion, in particular in a manner secured against rotation, on the retaining apparatus. A rotation of the optics unit about the first axis of rotation consequently leads to the optics unit, in particular the optics housing, being simultaneously rotated accordingly relative to the optical deflection element. This facilitates a particularly simple and stable structure and a further simplified operation of the observation instrument. Moreover, this facilitates the alignment of the stereo basis with the desired horizon by the user without modifying the viewing direction of the instrument determined by the deflection element.

Alternatively, the optical deflection element can be arranged so as to be rotatable relative to the retaining apparatus and to the optics unit, in particular relative to the optics housing; in particular, said optical deflection element can be rotatable about the first axis of rotation. By way of example, the optical deflection element can be arranged in a corresponding rotatable fashion on the retaining apparatus. This can provide an additional adjustment option for adjusting the viewing direction of the observation instrument and for choosing the object field.

Advantageously, the optical deflection element can be arranged on the retaining apparatus in such a way that it can be removed in part or in full by a user when they operate or configure the optical observation instrument. Such detachable fastening of the deflection element on the retaining apparatus can simplify the handling and cleaning of the observation instrument and can facilitate a use of the observation instrument even without the deflection element.

According to an advantageous embodiment of the invention, provision can be made for the optical deflection element to comprise a first and a second mirror element, wherein the second mirror element is arranged on the object side of the first mirror element such that the first and the second beam path extend over the first and the second mirror element and experience a respective deflection thereby. As a result of the successive deflections by the second and then by the first mirror element, the first and the second beam path are deflected from their respective viewing directions into the objective arrangement and hence into the first and the second stereo channel. The second mirror element is mounted in swivelable fashion about a swivel axis that is at least approximately perpendicular to the first axis of rotation. In particular, a mirror housing of the second mirror element can be mounted in rotatable fashion on a mirror housing of the first mirror element. The first and the second mirror element can each be embodied as obliquely arranged plane mirrors and can each be arranged to deflect the beam path through approximately 90°; thus, the plane mirror forming the first mirror element can be arranged, for example, obliquely at 45° with respect to the axis of the objective arrangement and can deflect a beam incident from the direction of the second axis of rotation into the axis of the objective arrangement, and the plane mirror forming the second mirror element can be arranged obliquely at approximately 45° with respect to the second axis of rotation. This can provide a further adjustment option for adjusting the viewing direction of the optical observation instrument, and so the observed object field can be altered without the spatial arrangement of the optics unit having to be altered in all cases. In the case where the first mirror element is mounted on the retaining apparatus so as to be rotatable about the first axis of rotation, it is possible to facilitate an adjustment of the viewing direction of the optical observation instrument about two axes and provide an additional adjustment option for choosing the object field.

According to a particularly preferred embodiment of the invention, the optics unit is rotationally coupled to an operating element that is rotatable about a second axis of rotation, wherein the second axis of rotation is directed at least approximately parallel to the viewing direction of the optical observation element. In particular, the rotatable operating element is arranged in such a way that the second axis of rotation approximately corresponds with the viewing axis or the angle bisector between the object-side sections of the first and the second beam path. Here, a deviation between the second axis of rotation and the viewing direction or the viewing axis is preferably as small as possible, although it can also be, for example, up to approximately 20° or, at most, up to approximately 45°. The operating element can, for example, be embodied as a rotary wheel or a rotary knob which is rotatable by hand such that rotating the operating element about the second axis of rotation allows the optics unit to be manually rotated about the first axis of rotation. According to this aspect of the invention, it has been recognized that a simple and intuitive operation of the optical observation instrument for the purposes of setting the alignment of the stereo basis is facilitated by virtue of the axis of rotation of the operating element being at least approximately parallel to the viewing direction or being in correspondence with the viewing axis.

In particularly advantageous fashion, the operating element can be arranged on a side opposite to the direction of the object field on the optical deflection element, for example on a mirror housing of the deflection element. This facilitates, firstly, simple and secure mechanical fastening of the rotatable operating element and, secondly, a particularly simple and intuitive operation.

Preferably, the rotatable operating element is rotationally coupled to the optics unit via a gearing. In particular, the gearing can comprise a first and a second gear or substantially consist of the first and the second gear, wherein the first gear is coupled to co-rotate with the rotatable operating element and the second gear, which meshes with the first gear, is coupled to co-rotate with the optics unit. Advantageously, the first and the second gear can each be embodied as a bevel gear. Consequently, the first gear can be rotated about the second axis of rotation by means of the operating element and the second gear can be rotated about the first axis of rotation together with the optics unit, and so rotating the operating element allows the optics unit to be rotated for the purposes of setting the stereo basis and for erecting the stereo half images. Particularly preferably, the first and the second gear can have the same number of teeth, wherein, further preferably, the diameter of the first and the second gear is approximately the same. As a result, rotating the rotatable operating element allows a rotation of the same magnitude to be carried out by the optics unit. As a result, the operation can be simplified further and designed more intuitively. In particular, the operation for aligning the stereo basis and for erecting the stereo image can be implemented in a way that corresponds to that of a generic optical observation instrument.

As an alternative or in addition thereto, provision can be made for the optics unit to be grasped by a user of the optical observation instrument and to be able to be rotated by hand about the first axis of rotation; by way of example, the optics housing can be directly grasped and rotated. An operating element configured as described above is not necessarily required in this case. As a result, a simple structure and, likewise, a simple operation of the optical observation instrument for the purposes of setting the alignment of the stereo basis can be facilitated.

Advantageously, a cover glass can be arranged on the object side of the deflection element. This can protect the deflection element from damage and contamination, for example against dust deposits or liquid splashes. In a further advantageous manner, the cover glass can be rotatable about the second axis of rotation and can be rotationally coupled to the rotatable operating element, for example by way of a connecting shaft that extends parallel to the second axis of rotation, said connecting shaft being driven by the second operating element and bringing about a corresponding rotation of the cover glass. By way of example, this can allow the attachment of additional optical elements on or in front of the cover glass on the object side and the co-rotation of these in the case of a change in the stereo basis. The cover glass can be arranged at an angle to the viewing axis of the optical observation instrument, in particular in order to avoid bothersome stray light.

Preferably, the optics unit comprises illumination optics for illuminating the object field with an illumination beam path that extends through the objective arrangement. The illumination optics can comprise a light source, such as, for instance, a light-emitting diode (LED), and collimator optics. On the other hand, the illumination optics can also be embodied, for instance, as a light connector for connecting an external light source by means of a light guiding cable to corresponding collimator optics. The objective arrangement can comprise a beam splitter for coupling the illumination radiation into the beam path of the optics unit, approximately in the direction of the axis of the objective arrangement, for the purposes of illuminating the object field, or the illumination radiation can be radiated, for example without a beam splitter, laterally into the objective arrangement, approximately in the direction of the object field. As a result of the illumination radiation emitted by the illumination optics being projected through the objective arrangement in the direction of the object field and consequently likewise being deflected by way of the deflection element, what can be achieved in a particularly simple manner is that the illumination radiation is always directed at the object field in every possible alignment of the optics unit and of the deflection element, provided the optical deflection element is rotatable for the purposes of altering the viewing direction.

Alternatively, the illumination optics can be arranged at the deflection element and an illumination beam path can be directed at the object field either directly or via a beam splitter. This can also facilitate an alignment of the illumination radiation on the object field.

Preferably, the retaining apparatus comprises a retaining bracket, which engages over the optics unit, wherein the deflection element is arranged at an object-side end of the retaining bracket. In particular, the retaining bracket can comprise a pivot bearing, at which the optics unit is mounted so as to be rotatable about the first axis of rotation, wherein the pivot bearing is arranged at the object-side end of the retaining bracket or of the optics unit and passed by the axis of the objective arrangement and by the first and the second beam path. The retaining bracket preferably engages over the optics unit in the longitudinal direction or along, or parallel to, the optical axis of the optics unit. The retaining bracket can comprise a further pivot bearing, which is arranged at the object-distant end of the retaining bracket or the optics unit and by means of which, for example, connecting cables can be guided, wherein the optics unit is mounted between the two pivot bearings so as to be rotatable about the first axis of rotation. By way of example, the pivot bearing or bearings can be embodied as a sliding bearing. In particular, the deflection element is arranged on the object side of the object-side pivot bearing and connected in rotatable or secured fashion to the retaining bracket. Alternatively, the retaining apparatus can be embodied, for example, as a tube or a shaft, within which the optics unit is received and rotatably mounted, wherein the first axis of rotation corresponds to the longitudinal axis of the tube or the shaft. Further alternatively, the retaining apparatus can comprise a rod, which extends at least in sections through the optics unit and on which the optics unit is rotatably mounted, wherein the first axis of rotation corresponds to the longitudinal axis of the rod. This can create a compact and robust holder for the optics unit.

A locking device, by means of which the optics unit or the optics housing is retained in a respective set rotational position, can advantageously be provided at the pivot bearing arranged at the object-side end of the retaining bracket or the optics unit and/or at the pivot bearing arranged at the object-distant end. By way of example, the locking device can be formed by frictional engagement of the pivot bearing or by a ratchet or a pawl. In the process, the pawl can, in particular, be spring-loaded in such a way that the optics unit is kept in the set rotational position by the spring force but the pawl is lifted from a corresponding notch against the spring force by a manual rotation of the optics unit.

More advantageously, the retaining apparatus can comprise a retaining angle brace, wherein the retaining bracket is arranged so as to be rotatable on the retaining angle brace. In particular, the retaining bracket is mounted so as to be rotatable on the retaining angle brace of the retaining apparatus in such a way that the optics unit is rotatable about a third axis, which is approximately perpendicular to the first axis of rotation and which moreover approximately extends through a center of gravity of the optics unit, the retaining bracket and further components arranged on the retaining bracket, for instance of the optical deflection element. Further preferably, the retaining apparatus comprises a retaining arm, wherein the retaining angle brace is arranged in rotatable and/or longitudinally displaceable fashion on the retaining arm. The retaining angle brace is, in particular, embodied and rotatably arranged on the retaining arm in such a way that an axis of rotation of the bearing of the retaining angle brace on the retaining arm is perpendicular to the third axis and intersects the latter approximately at the center of gravity of the optics unit, the retaining bracket and the further components arranged on the retaining bracket. This can facilitate a particularly simple adjustment of the position and orientation of the optics unit in space, with a small retaining force already being sufficient to retain the optics unit in a set orientation. Consequently, the optics unit can easily be brought into a relative position by the user and can be kept there by the retaining apparatus such that, firstly, an unimpeded observation of the operating field is facilitated and, secondly, the visual field of the user when gazing on a monitor is restricted to the smallest possible extent.

Alternatively, the retaining bracket can be arranged on the retaining arm, preferably be rotatably arranged on the retaining arm. In particular, by way of its object-distant end, the retaining bracket can be arranged on the retaining arm, wherein the retaining bracket is connected directly to the retaining arm or via a rotary joint. A retaining angle brace configured as described above is not required in this case.

Advantageously, the retaining apparatus can be embodied in such a way that a set position and/or orientation of the optics unit is fixable by nonpositive engagement, frictional engagement, interlocking engagement, in electromagnetic fashion and/or by a motor. In particular, provision can be made for an orientation of the optics unit relative to the retaining bracket, a rotational position of the retaining bracket relative to the retaining angle brace and/or a rotational position and/or displacement position of the retaining angle brace relative to the retaining arm to be able to be undertaken by hand and to be able to be held in fixed fashion by way of nonpositive engagement or else by means of an electromagnetic braking device. However, the retaining apparatus can also be embodied to be adjustable in motor-driven fashion in a corresponding way and the corresponding position or orientation of the optics unit can be fixable by a motor. As a result, a spatial position and viewing direction of the observation instrument as chosen by the user can be kept in a simple manner.

In general, rotating and retaining the optics unit for the purposes of setting the orientation of the stereo basis of the instrument can be implemented in manual or motor-driven fashion. Provided a motor rotates the unit and, in certain embodiments, also holds said unit in the set position, this rotation can also be implemented automatically by virtue of the relative position of the optics unit being captured by way of a relative position sensor. A signal of this sensor can be used by a controller to determine the relative position of the optics unit relative to the actual horizon, to the retaining arm, to the retaining apparatus or to the retaining bracket and then to rotate the optics unit in order to obtain a desired alignment of the stereo basis or a desired horizon when moving the instrument. To this end, the desired relative position can be determined automatically by the system or can be set by the user in advance or during use.

Preferably, the retaining arm is adjustable in motor-driven fashion and/or embodied as robotic retaining arm. Here, provision can be made for the retaining arm to be able to be operated by way of an operating apparatus such as, for instance, a joystick or else be operated by means of a robotic controller via a data connection, wherein the robotic controller can have a programmable configuration in order to bring the optics unit into a predeterminable position and/or orientation. The aforementioned rotation or automated rotation of the optics unit, and hence of the stereo basis, can alternatively or additionally be implemented by rotating parts of the robotic retaining arm, on which the retaining apparatus is fastened.

Further preferably, an operating device is arranged on or integrated in the retaining bracket, said operating device being able to comprise a plurality of operating buttons or other operating elements. Thus, for instance, provision can be made of a release button, which releases a fixation of the retaining arm and facilitates manual positioning. Here, the retaining arm can be configured and controllable in such a way that it always receives a weight of the optical observation instrument such that simple manual positioning is facilitated. Further, locking or fixation of the retaining arm can be triggered, for example by letting go of the release button. The operating device can comprise further operating elements, for example for controlling filters of the optics unit and/or for controlling illumination optics and/or for controlling camera and video functions, such as freeze frames or specific image modes for observing fluorescence. The buttons can be freely programmable in a manner known per se in order to be adapted to the requirements of the user.

The optical observation instrument can be connectable to an external control device, which is set up to supply power to and drive the at least one electronic image recorder and to display the recorded stereo image or to transfer corresponding image signals to a display device. By way of example, the control device can also be embodied for supplying and controlling an illumination device and/or for motor-driven movement of the retaining apparatus.

Preferably, the optical observation instrument or the external control device comprises an electronic processor device, which is set up to carry out mirroring and/or interchange, particularly preferably mirroring and interchange, of the stereo half images recorded by the at least one electronic image recorder. Mirroring the half images carried out electronically is advantageous, particularly in the case where the optical deflection element only has one or an odd number of reflecting surfaces successively arranged in the beam path. This can facilitate the generation of a stereo image and the display thereof for the user, said stereo image being adapted to the location of the user and imparting a spatial impression of the object field that can be intuitively grasped by the user.

The optical observation instrument is preferably embodied for observation of fluorescence, in particular for stereoscopic observation of fluorescence, and can, to this end, comprise one or more filters, which may be interchangeable, and, for example, four electronic image recorders.

An optical observation system according to the invention comprises an optical observation instrument and a control device connected to the latter, which are embodied as described above.

According to a method according to the invention for generating a stereo image of an object field, the optics unit of an optical observation instrument, embodied as described above, is brought into a spatial position. To this end, a user can grasp the retaining bracket, for example, and bring the latter manually into the desired position by adjusting the retaining apparatus; however, a motor-driven adjustment of the retaining apparatus may also be possible. Here, a viewing direction to an object field to be observed or a viewing axis can be set at the same time. Then, a stereo basis is aligned in accordance with the position of the user by a rotation of the optics unit about the first axis of rotation and the stereo half images are erected. To this end, a housing of the optics unit, for example, can be grasped by the user and manually rotated about the first axis of rotation; however, a rotatable operating element, which is arranged on the deflection element, the axis of rotation of which corresponds to the viewing axis and which is rotationally coupled to the optics unit, can optionally also be rotated by the user. Preferably, electronic mirroring and/or interchanging of the stereo half images recorded by the at least one electronic image recorder is carried out by means of an electronic processor device, which can be assigned to the observation instrument or an external control device. The possibly mirrored and/or interchanged stereo half images are subsequently displayed for the user on a display device which is suitable for stereoscopic display.

It is self-evident that the features mentioned above and the features yet to be discussed below may be used not only in the respectively specified combination but also in other combinations or individually without departing from the scope of the present invention.

BRIEF DESCRIPTION OF THE DRAWINGS

Further aspects of the invention arise from the following description of preferred exemplary embodiments and the attached drawing. In detail:

FIG. 8 shows a side view of a fourth exemplary embodiment of an optical observation instrument according to the invention.

DETAILED DESCRIPTION

Figure 1:
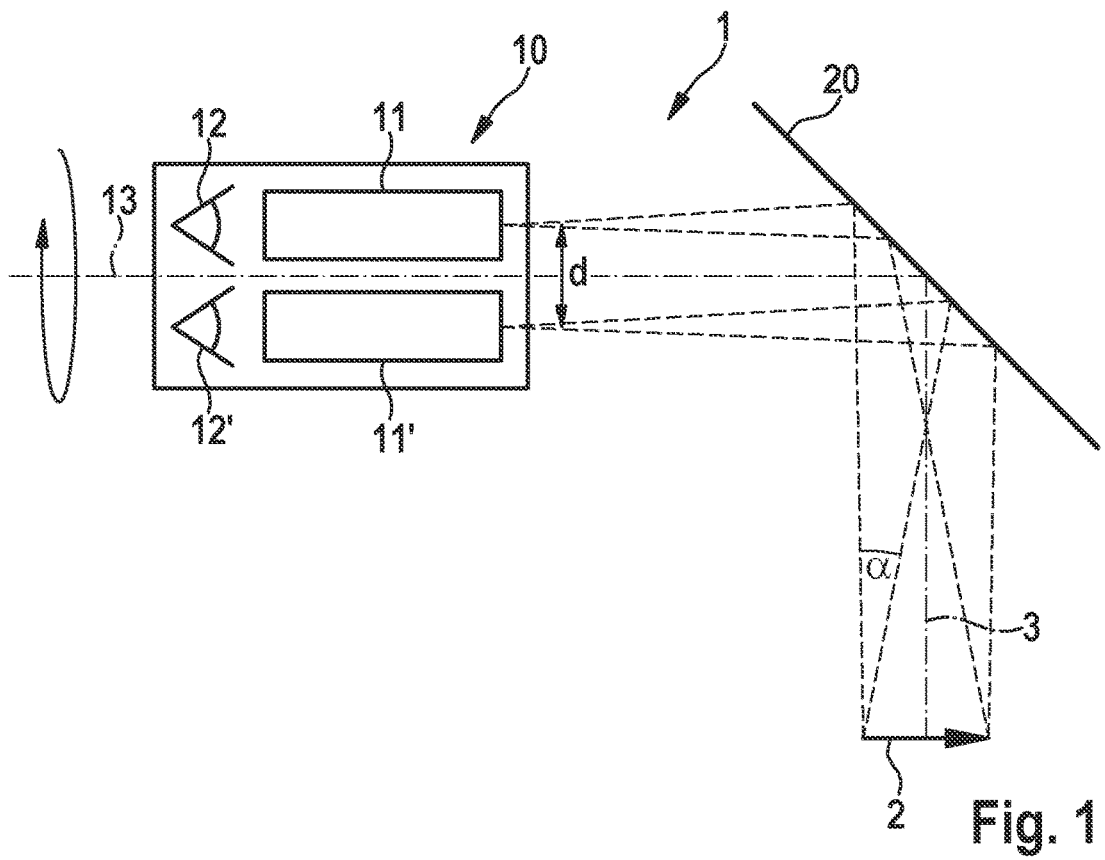
FIG. 1 shows an exemplary schematic sketch of an optical observation instrument according to the invention.

FIG. 1 shows a basic schematic diagram of an exemplary embodiment of an optical observation instrument according to the invention. The optical observation instrument 1 comprises an optics unit 10, which has two stereo channels 11, 11' which each comprise an objective and which each have assigned an electronic image recorder 12, 12' in the example illustrated. The stereo channels 11, 11' can comprise further optical elements. The stereo channels 11, 11' are illustrated separately from one another in FIG. 1; however, the stereo channels 11, 11' or the objectives thereof can also comprise common optical elements, for example a common front lens (see below). The objectives of the stereo channels 11, 11' each generate an image of an object 2, arranged in an object field, on the respective image recorder 12, 12', with the respective beam paths only being illustrated in part in FIG. 1. The optics unit 10 is mounted so as to be rotatable about a first axis of rotation 13, the latter corresponding to an axis of the objective arrangement of the optics unit 10 and being a center axis between the optical axes of the objectives of the stereo channels 11, 11' in the example shown. The stereo channels 11, 11' are offset with respect to one another transversely to the first axis of rotation 13, with the offset of the optical axes representing the stereo basis d of the observation instrument 1.

To deflect the beams incident from the direction of the object 2 into the stereo channels 11, 11' or into the respective objectives, the optical observation instrument 1 comprises a deflection mirror 20, which is embodied as a plane mirror and at which the beams are respectively reflected once and deflected to the objectives of the stereo channels 11, 11'. The viewing directions of the two stereo channels 11, 11' differ by a stereo angle α, which is indicated in FIG. 1 between two beams that emanate from the same point on the object 2 and which are deflected into the objectives of the stereo channels 11, 11' by the deflection mirror 20; the viewing directions of the stereo channels 11, 11' might also be parallel to one another (not illustrated), however. The deflection mirror 20 is inclined by 45° with respect to the first axis of rotation 13, wherein the object-side beam paths of the two stereo channels 11, 11' are deflected into the respective objectives at different rotational positions of the optics unit 10 by way of the face of the deflection mirror 20. The viewing axis 3 corresponds to an angle bisector between the object-side sections of the beam paths of the two stereo channels 11, 11' and is angled by 90° with respect to the first axis of rotation 13. The viewing direction of the observation instrument 1 is a mean viewing direction between the viewing directions of the stereo channels 11, 11', wherein the viewing axis 3 can be considered to be, for example, an object-side continuation, deflected by the deflection mirror 20, of the center axis between the optical axes of the objectives of the stereo channels 11, 11'. A beam incident on the deflection mirror 20 along the viewing axis 3 from the object 2 is deflected into the center axis, i.e., into the first axis of rotation 13, in the example shown, wherein this beam however does not reach one of the stereo channels 11, 11'. By rotating the optics unit 10 about the first axis of rotation 13, it is possible to alter the direction of the stereo basis d in order to adapt the latter to the position of a user who observes the stereo half images recorded by the image recorders 12, 12' and in order to erect the displayed stereo image accordingly.

Figure 2:
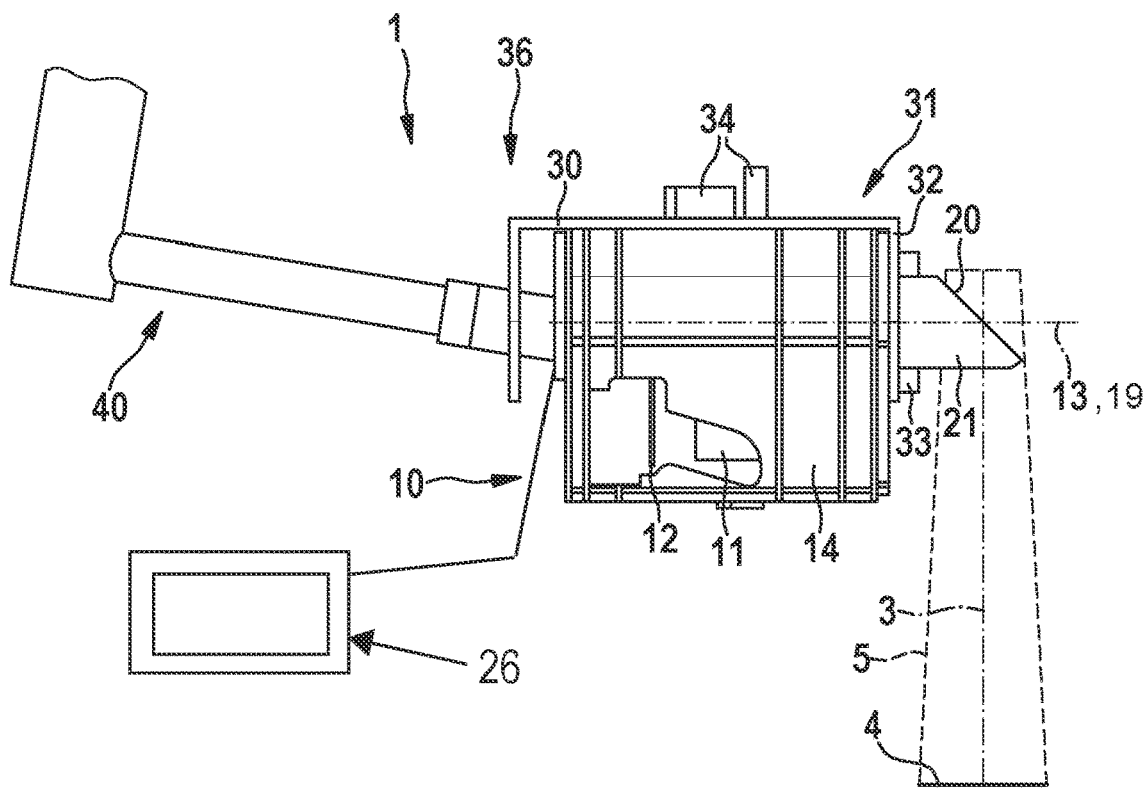
FIG. 2 shows a side view of a first exemplary embodiment of an optical observation instrument according to the invention.

FIG. 2 shows a partly cut open side view of a first exemplary embodiment of the optical observation instrument according to the invention. According to the first exemplary embodiment, the observation instrument 1 is an operating microscope; this also holds true in the further exemplary embodiments. The optics unit 10 corresponds to the microscope body of the surgical microscope. The optics unit 10 comprises an optics housing 14, within which optical and electronic components are received; in FIG. 2, optical components of a stereo channel 11 and an electronic image recorder 12 are indicated.

As may be identified in FIG. 2, the microscope body of the surgical microscope, i.e., the optics unit 10, is held in rotatable fashion in a retaining bracket 30. At the object-side end 31 of the retaining bracket 30, the latter comprises a plate 32, on which the optics unit 10 is mounted in a pivot bearing 33 so as to be rotatable about the first axis of rotation 13. Here, the beam paths of the two stereo channels 11, 11' (see FIG. 1) extend through the pivot bearing 33. At the object-distant end 36 of the retaining bracket 30, which is opposite to the object-side end 31, said retaining bracket is connected to a retaining arm 40, which consists of a plurality of sections that are angled with respect to one another and possibly adjustable with respect to one another. By way of example, the retaining arm 40 can be embodied as a stand, which can be fastened to an operating table or which can also stand independently of the operating table; however, it might also be a robotic retaining arm, for example. The retaining bracket 30 can be connected in rotatable and/or swivelable fashion to the retaining arm 40. Supply and signal lines that connect the optics unit 10 to an external control device can extend through the retaining arm 40. The retaining bracket 30 can comprise fastening elements 34 for fastening a handle (not illustrated) in order to facilitate a manual adjustment of the retaining arm 40 for the purposes of choosing a position and orientation of the retaining bracket 30.

Further on the object side, the deflection mirror 20 is arranged on the plate 32, said deflection mirror 20 being at a 45° angle to the first axis of rotation in the example shown. The deflection mirror 20 is held in a mirror housing 21, which is arranged on the object-side of the bearing 33. In the example shown, the mirror housing 21 with the deflection mirror 20 is arranged on the plate 32 so as to be rotatable about the first axis of rotation 13; however, it can also be connected so as to co-rotate with the plate 32. In FIG. 2, the viewing axis 3, which defines the viewing direction of the surgical microscope, the object field 4 and a cone 5 are indicated, the latter comprising the object-side sections of the beam paths of the two stereo channels 11, 11' (see FIG. 1), including a virtual extension beyond the deflection mirror 20.

Figure 3:
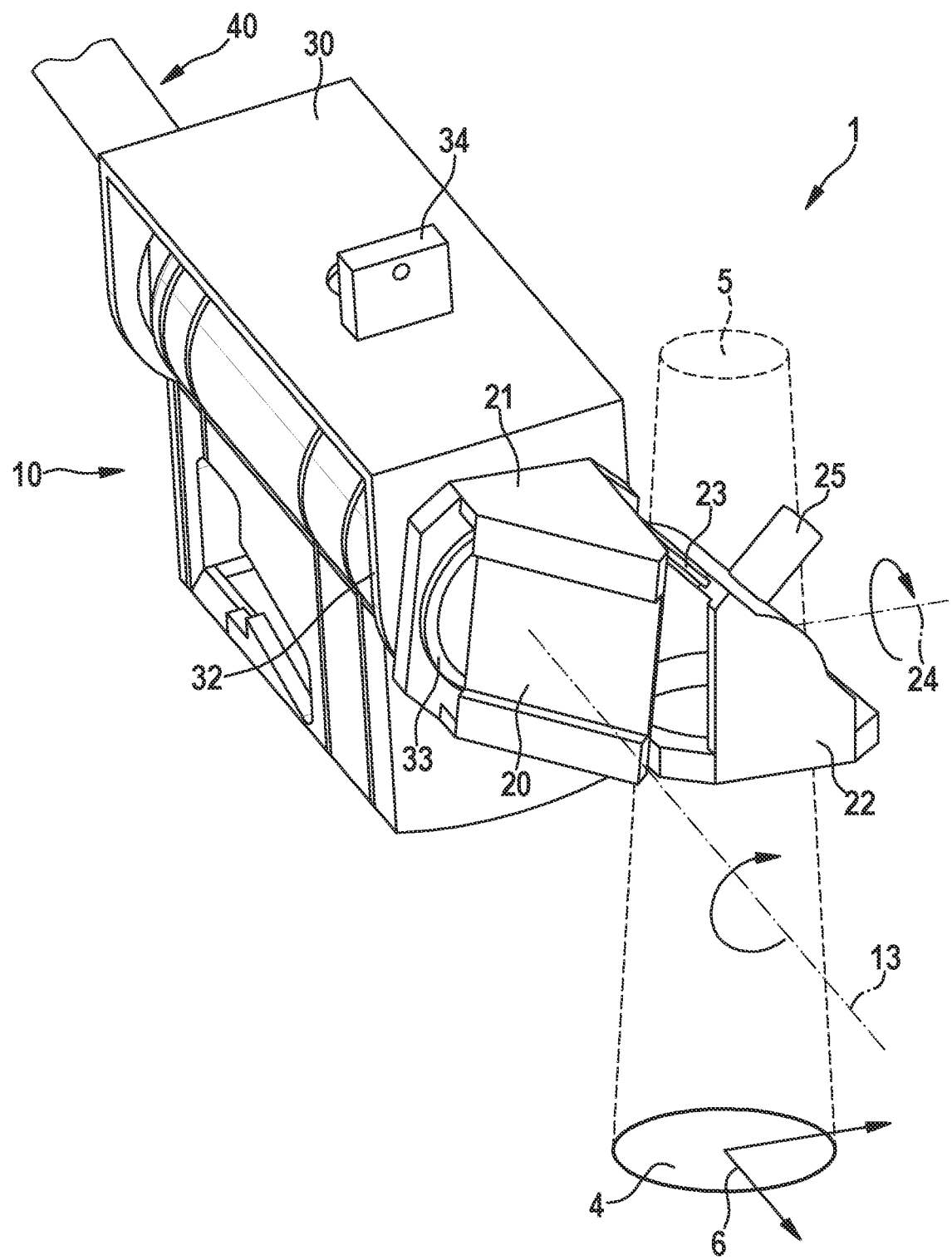
FIG. 3 shows an oblique view of a second exemplary embodiment of an optical observation instrument according to the invention.

FIG. 3 illustrates a partly cut open oblique view of a second exemplary embodiment of the optical observation instrument according to the invention. According to this exemplary embodiment, the observation instrument 1 comprises an optics unit 10, a retaining bracket 30 and a retaining arm 40, which are embodied as described in relation to FIG. 2. The pivot bearing 33 for rotatable bearing of the optics unit 10 is arranged on the object-side plate 32 of the retaining bracket 30, wherein a first mirror housing 21 with the first deflection mirror 20 is arranged at the pivot bearing 33 on the object side.

According to the second exemplary embodiment shown in FIG. 3, the mirror housing 21 is likewise mounted so as to be rotatable about the first axis of rotation 13. Further, a second mirror housing 22 with a second deflection mirror 23 is arranged on the object-side side of the first mirror housing 21 in the beam path. As indicated in FIG. 3, the second mirror housing 22 is retained at the first mirror housing 21 and rotatable relative to the first mirror housing 21 about a swivel axis 24, which is perpendicular to the first axis of rotation 13. A handle element 25 for manually adjusting the first and the second deflection mirror 20, 23 is provided at the second mirror housing 22.

Beams incident from the object field 4 within the cone 5 are deflected approximately in the direction of the swivel axis 24 to the first deflection mirror 20 by the second deflection mirror 23 and are deflected there approximately in the direction of the first axis of rotation 13 to the optics unit 10. The object-side sections of the beam paths of the first and of the second stereo channel are consequently each deflected twice through approximately 90°. By rotating the first deflection mirror and the second deflection mirror 23, it is possible to alter the viewing 20 direction of the observation instrument 1 in such a way that the observable object field 4 can be displaced in two directions (indicated by the arrows 6 in FIG. 3).

FIGS. 4 to 7 illustrate a third exemplary embodiment of an optical observation instrument according to the invention in different views.

Figure 4:
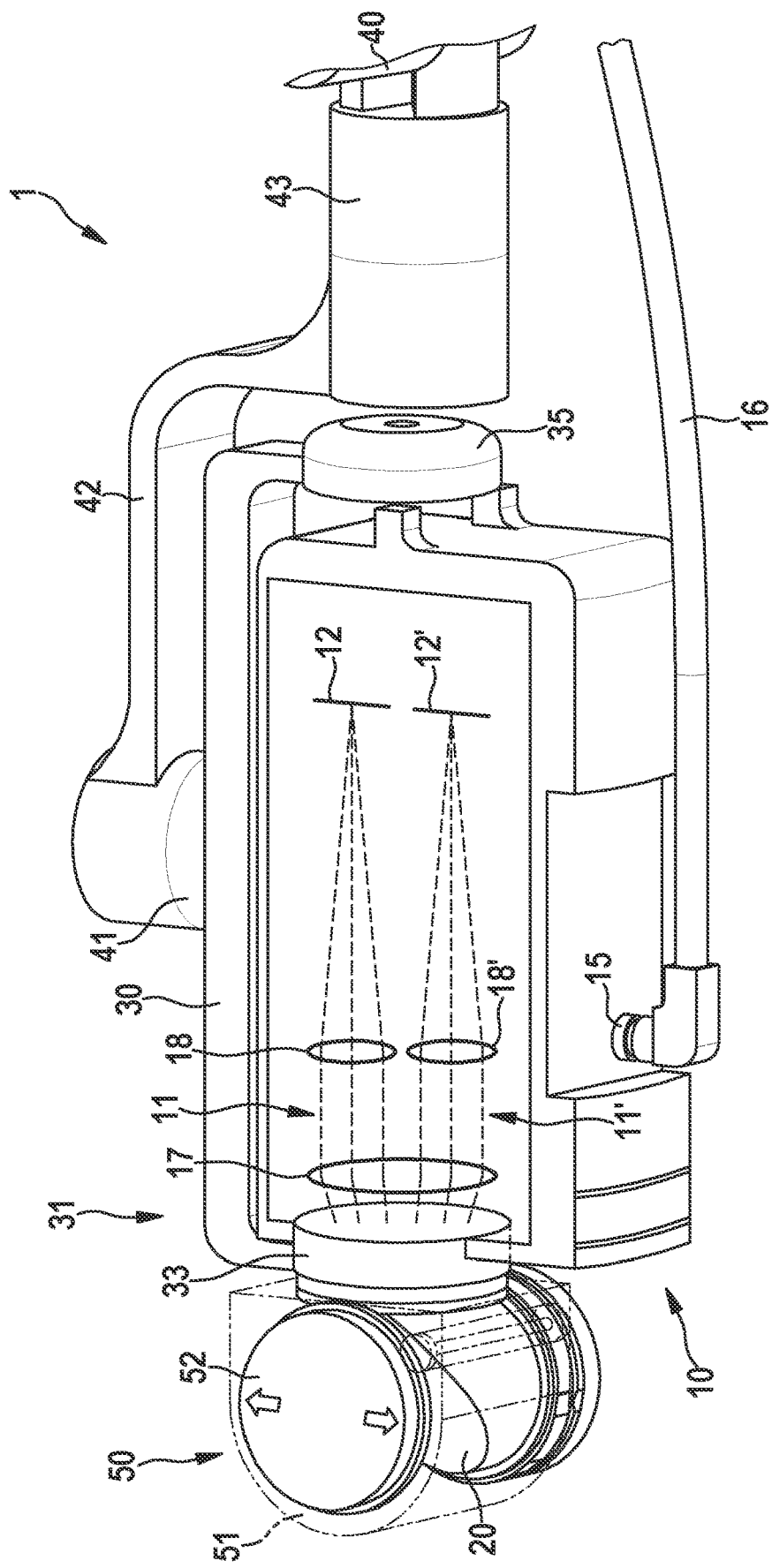
FIG. 4 shows a partly cut open side view of a third exemplary embodiment of an optical observation instrument according to the invention.

According to the third exemplary embodiment, the optical observation instrument 1, which is likewise a surgical microscope, comprises an optics unit 10 which is configured as described above but, as shown in FIG. 4, comprises a lateral connection 15 for connecting a cable 16, by means of which an illumination device of the optics unit 10, not illustrated in any more detail, can be supplied with electrical or optical power. Further, the cable 16 can serve to establish a connection to an external control device for supplying power to, controlling and/or transferring signals of the electronic image recorders and optionally further electrical or electronic components of the optics unit 10. A front lens 17, through which the beam paths of the first and the second stereo channel 11, 11' (see FIG. 1) extend, is arranged in the vicinity of the pivot bearing 33. The front lens 17 forms a common optical element of an objective arrangement which comprises further optical elements, in particular the further objective lenses 18, 18', which are illustrated symbolically in FIG. 4 and which are each assigned to one of the stereo channels 11, 11'. The objective arrangement, which is illustrated in simplified fashion in FIG. 4, can comprise optionally further objective lenses and/or optical elements in addition to the front lens 17 and the objective lenses 18, 18'. The objective arrangement is embodied to generate an image of the object field on the electronic image recorders 12, 12' in each case. As shown in FIG. 4 in exemplary fashion, the beam paths of the stereo channels 11, 11' can extend approximately parallel to one another after the passage through the front lens 17. The optics unit 10 can comprise further optical components, for instance filters, deflection elements and/or electromechanical components, which are not shown in FIG. 4; the housing of the optics unit 10 is not illustrated in FIG. 4 either. The objective arrangement of the first and the second exemplary embodiment can be constructed in the same way as in the third exemplary embodiment.

The optics unit 10 is mounted so as to be rotatable on the retaining bracket 30 by means of the pivot bearing 33 and the further pivot bearing 35. The retaining bracket 30 is mounted so as to be rotatable and virtually in the center on a retaining angle brace 42 by means of a pivot bearing 41, said retaining angle brace 42 being mounted on the retaining arm 40 by means of a further pivot bearing 43; moreover, the retaining angle brace 42 is held in longitudinally displaceable fashion on the retaining arm 40. The axes of rotation of the pivot bearing 41 and of the further pivot bearing 43 are perpendicular to one another and extend approximately through the center of gravity of the components arranged on the retaining arm, specifically the retaining bracket 30, the optics unit 10 and the subsequently described operating unit 50. The first axis of rotation, about which the optics unit 10 is mounted in the retaining bracket 30 so as to be rotatable, can be flush with the axis of rotation of the further pivot bearing 43 in the case of a corresponding position of the pivot bearing 41.

The operating unit 50 comprises a housing 51, which is arranged in a manner secured against rotation on the plate 32 on the object-side end 31 of the retaining bracket 30 in the region of the pivot bearing 33; however, the operating unit can also be mounted on the retaining bracket 30 so as to be rotatable about the first axis of rotation 13, about which the optics unit 10 is rotatable. Arranged within the housing 51 of the operating unit 50 there is a deflection mirror 20 that is stationary relative to the housing 51, said deflection mirror being embodied as a plane mirror and serving to deflect the first and the second beam path from the object field to the front lens 17 and into the first and the second stereo channel 11, 11' or into the further objective lenses 18, 18'. A rotary wheel 52 is arranged at the side of the housing 51 opposite to the object field, the axis of rotation of said rotary wheel corresponding to the viewing axis of the observation instrument. When the observation instrument 1 is positioned above the object field to be observed, the rotary wheel 52 is consequently arranged on the top side of the housing 51. As described in more detail below, the optics unit 10 can be rotated about the first axis of rotation 13 by means of the rotary wheel 52. On the object-side side of the housing 51, i.e., on the lower side thereof in the aforementioned sense, said housing is terminated by a transparent cover glass 53 (see FIG. 7). The cover glass 53 can be rotatable by means of a connecting shaft 54, which transfers a rotation of the rotary wheel 52 to the cover glass 53.

Figure 5:
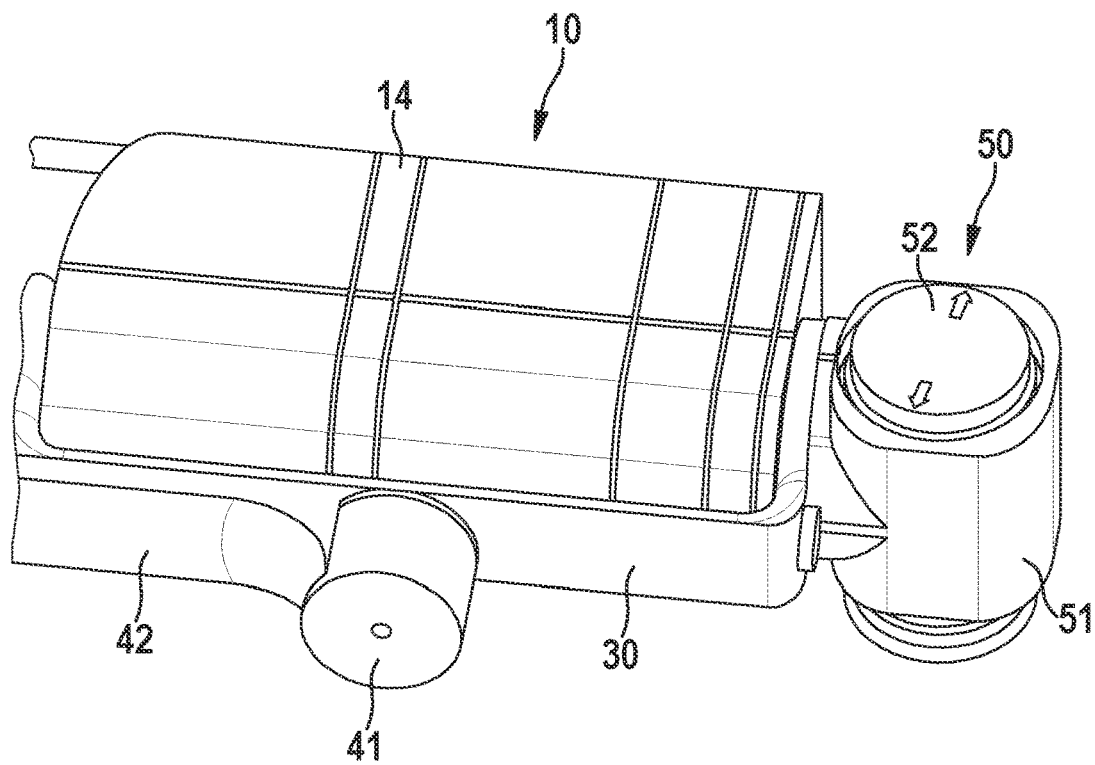
FIG. 5 shows a further side view of the optical observation instrument as per FIG. 4.

FIG. 5 shows the optical observation instrument 1 according to the third exemplary embodiment in a further side view, wherein the retaining angle brace 42 with the pivot bearing 41, on which the retaining bracket 30 is mounted, is identifiable. Furthermore, the optics unit 10 with the optics housing 14 and the operating unit 50 with its housing 51 and the rotary wheel 52 are illustrated.

Figure 6:
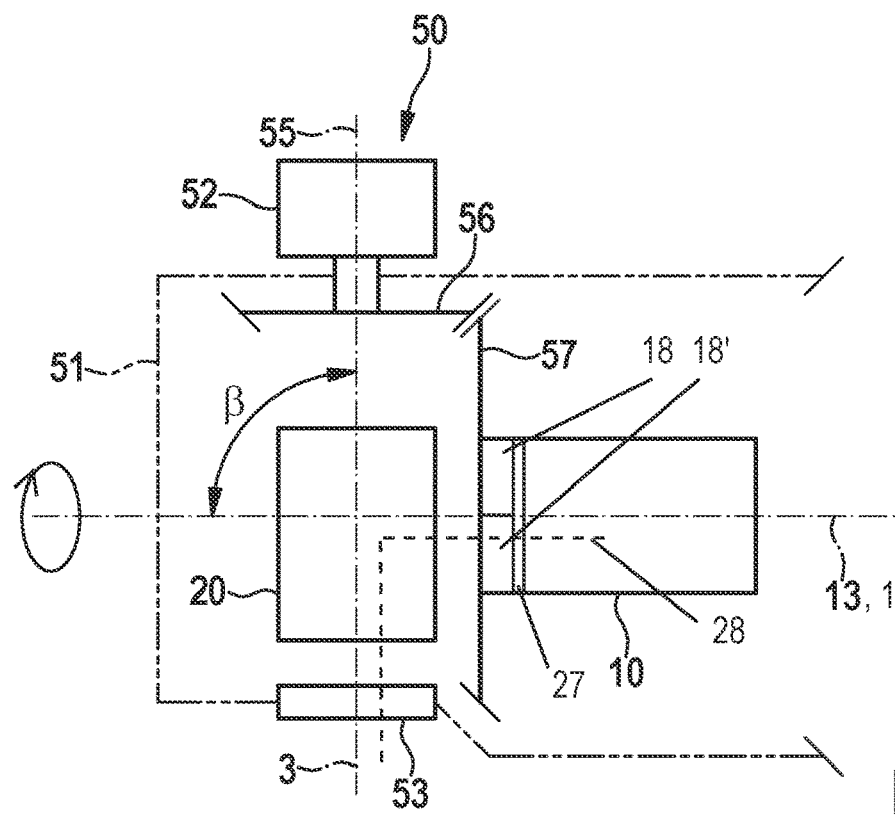
FIG. 6 shows a schematic diagram of the adjustment mechanism of the optical observation instrument as per FIG. 4.

FIG. 6 shows the gearing used to transfer a rotation of the rotary wheel 52 for rotating the optics unit 10 to the latter in a schematic diagram. As illustrated symbolically in FIG. 6, the deflection mirror 20 is received in stationary fashion in the housing 51 of the operating unit 50. The rotary wheel 52 is arranged on the upper side of the housing 51 and is rotatable about an axis of rotation 55, which is flush with the viewing axis 3 of the optical observation instrument. A first gear 56 is arranged in rotatable fashion on the axis of rotation 55 and is connected so as to co-rotate with the rotary wheel 52. The optics unit 10 is mounted so as to be rotatable about the first axis of rotation 13 within the retaining bracket 30 (see FIGS. 4 and 5) which is not illustrated here. A second gear 57, which is connected so as to co-rotate with the optics unit 10, is arranged on the first axis of rotation 13. The second gear 57 meshes with the first gear 56 such that a rotation of the rotary wheel 52 about its axis of rotation 55 is transferred into a rotation of the optics unit 10 about the first axis of rotation 13. The first and the second gear 56, 57 have the same number of teeth and approximately the same diameter, and so a rotation of the rotary wheel 52 is transferred into an equal rotation of the optics unit 10. Preferably, the first and the second gear 56, 57 can be embodied as bevel gears. The housing 51 of the operating unit 50 can be configured as shown in FIGS. 4, 5 and 7, although it can also surround the optics unit 10 according to a variant of the third exemplary embodiment and for example replace the retaining bracket 30.

As described above, the beam paths of the first and the second stereo channel 11, 11' are deflected by the deflection mirror 20 to the front lens 17 of the optics unit 10 and extend through the second gear 57. In the example shown, the viewing axis 3 forms an angle $\beta=90°$ with the first axis of rotation 13 and the first and the second beam path, which can each deviate by half the stereo angle $\alpha$ from the viewing axis 3 and the first axis of rotation 13, respectively, are each deflected through approximately 90° at the deflection mirror. The objective lenses 18, 18' are part of the optics unit 10. The axis 19 of the objective arrangement in this case is identical to the axis of rotation 13 of the optics unit 10. Here, an illumination beam path 28 is shown schematically. The beam path 28 runs from an illumination source, which is not depicted here, through the objective arrangement and the illumination optics 27. It is then deflected by mirror 20 in the direction of the viewing axis 3 and runs through cover glass 53, in order to illuminate the objective field 4.

Figure 7:
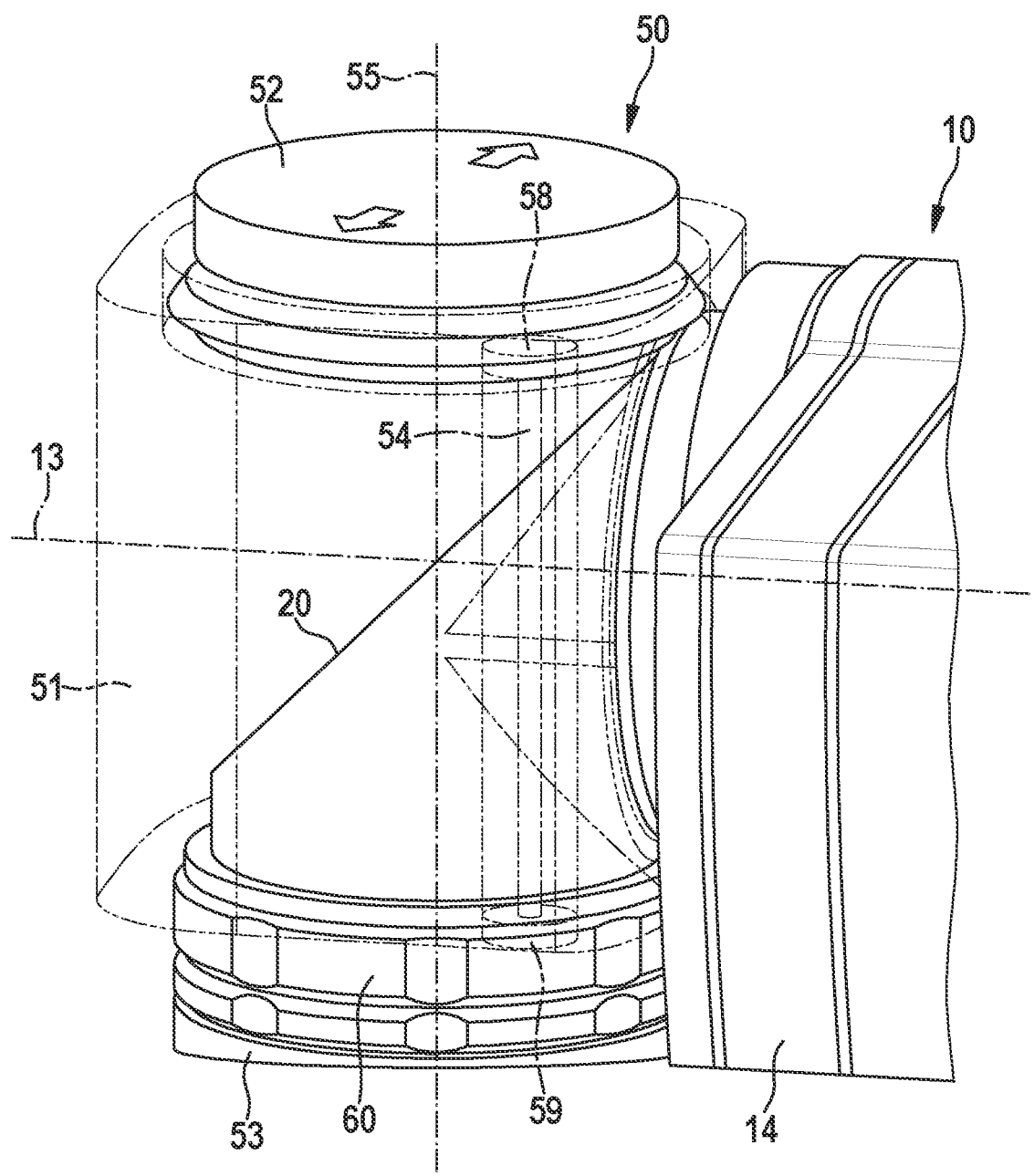
FIG. 7 shows a partly transparent partial view of the adjustment mechanism of the optical observation instrument as per FIG. 4.

As shown in FIG. 7, the operating unit 50 can comprise a connecting shaft 54 extending parallel to the axis of rotation 55 of the rotary wheel 52, said connecting shaft being driven by the rotary wheel 52 via a gear 58 and driving a rotary ring 60 via a further gear 59, the cover glass 53 being held on said rotary ring. In the case of a rotation of the rotary wheel 52 and of the optics unit 10, this can simultaneously bring about a corresponding, preferably equal rotation of the cover glass 53.

FIG. 8 illustrates a side view of a fourth exemplary embodiment of an optical observation instrument according to the invention. In this exemplary embodiment, the retaining bracket 30, in which the optics unit 10 is mounted in rotatable fashion, is securely connected at its object-distant end 36 to a robotic retaining arm, not illustrated. The robotic retaining arm is drivable in such a way that it takes the weight of the optical observation instrument 1, independently of a position and orientation of the latter, and fixes a set position and orientation of the retaining bracket 30.

Integrated in the retaining bracket 30 is an operating device 37, which comprises, on its top side, a plurality of operating buttons 38 for controlling, e.g., a light source or filters, which are arranged in the optics unit 10. A release button 39 is arranged on the lower side opposite to the operating buttons 38 and, in particular, to a finger rest between the operating buttons. Pressing the release button 39 releases the fixation of the position and orientation of the retaining bracket 30, with the weight of the optical observation instrument still being carried by the robotic retaining arm; now, the retaining bracket 30 can be brought manually into a new position and orientation. The fixation of the position and orientation of the retaining bracket 30 is reactivated by letting go of the release button 39. In addition or as an alternative thereto, the release can relate to the robotic retaining arm, which transitions into a floating-holding state by operating the release button 39, in which state the hinges of the arm are partly released but hold the weight of the optical observation instrument 1 such that the latter maintains its position. The arm with the instrument 1 can then be moved freely by the user. By letting go of the release button 39, the retaining arm is locked again in the set position.

To alter the rotational position of the optics unit 10, and hence to adapt the stereo basis or the horizon, the housing 14 of the optics unit 10 can be grasped by the user and rotated manually. A set rotational position is retained by a latching mechanism, in this case ratchet 44, which is arranged on the pivot bearing 35. The latching mechanism comprises, for example, a pawl which is mounted in the optics unit 10 and which engages in spring-loaded fashion in latching notches of a gear securely connected to the retaining bracket 30; when rotating the optics unit 10 manually, the spring force is overcome and the pawl is lifted from a respective latching notch such that the optics unit 10 can be rotated relative to the retaining bracket 30 about the first axis of rotation 13. Proceeding from the upright position illustrated in FIG. 8, the optics unit 10 can be rotated through respectively 135° in both directions about the axis of rotation 13.

The deflection mirror, not illustrated, is securely arranged in the mirror housing 21, which is securely connected to the retaining bracket 30 or which can have a top side formed in one piece with the latter. The housing 14 of the optics unit comprises further operating elements and a connector 15 for a cable. Otherwise, the fourth exemplary embodiment is embodied as described above, in particular in accordance with the first exemplary embodiment.

According to a method according to the invention, the optics unit 10 arranged on the retaining arm 40 or on the retaining bracket 30 is brought into a desired spatial position by a user, for example by hand by means of a handle arranged on the retaining bracket 30 or else in motor-driven fashion by controlling appropriate actuators by means of an external control device that has been set up to this end. As a result, it is possible to simultaneously set a viewing direction or a viewing axis 3 to an object field 4 to be observed; the viewing direction can additionally be altered in one or two degrees of freedom by rotating the mirror housing 21 in the exemplary embodiment in accordance with FIG. 2 or by rotating the mirrors housings 21, 22 in the exemplary embodiment in accordance with FIG. 3. In the exemplary embodiments as per FIG. 2 and FIG. 3, the optics unit 10 can thereupon be grasped by the user and manually rotated about the first axis of rotation 13 for the purposes of setting the direction of the stereo basis. In the exemplary embodiment in accordance with FIGS. 4 to 7, the stereo basis can be set manually by a rotation of the rotary wheel 52, which brings about a corresponding rotation of the optics unit 10. By means of a processor device, which can be arranged, for example, in the optics unit 10 as processor 45, or in an external control device, it is possible to undertake electronic mirroring of the stereo half images recorded by the image recorders 12, 12'. Additionally, the stereo half images recorded by the image recorders 12, 12' can be interchanged in electronic fashion. The half images processed thus are subsequently displayed on a display device such as a monitor 26 set up for a stereoscopic display, which can be connected to the instrument and/or the external control device. In this way, it is possible to generate and display a stereo image, which provides the user with an intuitively graspable spatial impression of the object field 4.

Not all reference signs have been presented in all figures for reasons of clarity. Reference signs not explained in relation to one figure have the same meaning as in the other figures.

LIST OF REFERENCE SIGNS

1 Optical observation instrument
2 Object
3 Viewing axis
4 Object field
5 Cone
6 Arrow
10 Optics unit
11, 11' Stereo channel
12, 12' Image recorder
13 First axis of rotation
14 Housing
15 Connector
16 Cable
17 Front lens
18, 18' Objective lens
19 Axis of the objective arrangement
20 Deflection mirror
21 Mirror housing
22 Mirror housing
23 Deflection mirror
24 Swivel axis
25 Handle element
26 Monitor
27 illumination optics
28 illumination beam path
30 Retaining bracket 31 Object-side end
32 Plate
33 Pivot bearing
34 Fastening element
35 Pivot bearing
36 Object-distant end
37 Operating device
38 Operating buttons
39 Release button
40 Retaining arm
41 Pivot bearing
42 Retaining angle brace
43 Pivot bearing
44 ratchet
45 processor
50 Operating unit
51 Housing
52 Rotary wheel
53 Cover glass
54 Connecting shaft
55 Axis of rotation
56 Gear
57 Gear
58 Gear
59 Gear
60 Rotary ring

The invention claimed is:

1. An optical observation instrument comprising:
an optics unit with an objective arrangement and at least one electronic image recorder, wherein the optics unit has a first stereo channel with a first beam path and a second stereo channel with a second beam path, the optics unit configured for recording a stereo image of an object field with the at least one electronic image recorder, and wherein the first and the second beam paths extend through the objective arrangement, and
a retaining apparatus, on which the optics unit is mounted, the optics unit rotatable about the objective arrangement, wherein the retaining apparatus comprises a retaining bracket, which a first axis of rotation, the first axis of rotation at least approximately corresponding to an axis of the objective arrangement, wherein the retaining apparatus comprises a retaining bracket, which engages over the optics units, which is arranged inside a housing, and on which the optics unit is mounted to be rotatable about the first axis of rotation, wherein an optical deflection element is retained at an object-side end of the retaining bracket, and wherein the optical observation instrument has a viewing direction that is angled in relation to the axis of the objective arrangement and comprises the optical deflection element, arranged on an object-side of the objective arrangement, and configured to deflect the first and the second beam paths into the objective arrangement.

2. The optical observation instrument as claimed in claim 1, wherein the viewing direction is angled through approximately 90° in relation to the axis of the objective arrangement.

3. The optical observation instrument as claimed in claim 1, wherein the optics unit is mounted to be rotatable relative to the retaining apparatus and relative to the optical deflection element about the first axis of rotation.

4. The optical observation instrument as claimed in claim 1, wherein the optics unit has an elongated optics housing, which extends at least approximately in the direction of the axis of the objective arrangement.

5. The optical observation instrument as claimed in claim 1, wherein the objective arrangement comprises an object-side front lens, wherein the first and the second beam path extend through the front lens.

6. The optical observation instrument as claimed in claim 1, wherein the optical deflection element comprises a plane mirror at an angle to the axis of the objective arrangement.

7. The optical observation instrument as claimed in claim 1, wherein the optical deflection element is arranged on the retaining apparatus in a manner secured against rotation.

8. The optical observation instrument as claimed in claim 1, wherein the optics unit is rotationally coupled with an operating element that is rotatable about a second axis of rotation, wherein the second axis of rotation is directed at least approximately parallel to the viewing direction.

9. The optical observation instrument as claimed in claim 8, wherein the rotatable operating element is arranged at the optical deflection element on a side opposite to the object field.

10. The optical observation instrument as claimed in claim 1, wherein a cover glass is arranged on an object side of the optical deflection element.

11. The optical observation instrument as claimed in claim 1, wherein the optics unit comprises illumination optics configured to illuminate the object field with an illumination beam path that extends through the objective arrangement.

12. The optical observation instrument as claimed in claim 1 wherein the retaining apparatus comprises a retaining angle brace and a retaining arm, wherein the retaining bracket is arranged in rotatable fashion at the retaining angle brace, which is arranged in rotatable and/or longitudinally displaceable fashion at the retaining arm.

13. The optical observation instrument as claimed in claim 1, wherein the retaining apparatus comprises a retaining arm, wherein the retaining bracket is arranged in rotatable fashion at the retaining arm.

14. The optical observation instrument as claimed in claim 1, wherein the retaining apparatus is configured such that one or more of a position and orientation of the optics unit is fixable by one or more of: nonpositive engagement, frictional engagement, interlocking engagement, an electromagnetic mechanism, and by a motor.

15. The optical observation instrument as claimed in claim 1, wherein the optical observation instrument comprises a processor device, which is configured for mirroring and/or interchanging the stereo half images.

16. The optical observation instrument as claimed in claim 1, wherein the optical observation instrument is a surgical microscope or exoscope.

17. A method to generate a stereo image of an object field comprising:
bringing an optics unit of an optical observation instrument into a spatial position, the optics unit including an objective arrangement and at least one electronic image recorder, wherein the optics unit has a first stereo channel with a first beam path and a second stereo channel with a second beam path, the optics unit configured for recording a stereo image of an object field with the at least one electronic image recorder, and wherein the first and the second beam paths extend through the objective arrangement, and a retaining apparatus, on which the optics unit is mounted, the optics unit rotatable about a first axis of rotation, the first axis of rotation at least approximately corresponding to an axis of the objective arrangement, wherein the retaining apparatus comprises a retaining bracket, which engages over the optics unit, which is arranged inside a housing, and on which the optics unit is mounted to be a rotatable about the first axis of rotation, wherein a optical deflection element is retained at an object-side end of the retaining bracket, and wherein the optical observation instrument has a viewing direction that is angled in relation to the axis of the objective arrangement and comprises the deflection element, arranged on an object-side of the objective arrangement, and configured to deflect the first and the second beam paths into the objective arrangement, setting a viewing direction to the object field, setting an alignment of a stereo basis by rotating the optics unit about the first axis of rotation, recording stereo half images by the at least one electronic image recorder of the optical observation instrument, and displaying the stereo half images on a display device.

18. The method of claim 17, wherein the optical observation instrument is a surgical microscope or exoscope.

19. An optical observation instrument comprising:

an optics unit with an objective arrangement and at least one electronic image recorder, wherein the optics unit has a first stereo channel with a first beam path and a second stereo channel with a second beam path, the optics unit configured for recording a stereo image of an object field with the at least one electronic image recorder, and wherein the first and the second beam paths extend through the objective arrangement, and a retaining apparatus, on which the optics unit is mounted, the optics unit rotatable about a first axis of rotation, the first axis of rotation at least approximately corresponding to an axis of the objective arrangement, wherein the retaining apparatus comprises a retaining bracket, the retaining bracket engages over a housing that includes the optics unit, the optics unit being mounted to the housing and rotatable about the first axis of rotation, wherein an optical deflection element is retained at an object-side end of the retaining bracket, and wherein the optical observation instrument has a viewing direction that is angled in relation to the axis of the objective arrangement and comprises the optical deflection element, arranged on an object-side of the objective arrangement, and configured to deflect the first and the second beam paths into the objective arrangement.

20. A method to generate a stereo image of an object field comprising:

bringing an optics unit of an optical observation instrument into a spatial position, the optics unit including an objective arrangement and at least one electronic image recorder, wherein the optics unit has a first stereo channel with a first beam path and a second stereo channel with a second beam path, the optics unit configured for recording a stereo image of an object field with the at least one electronic image recorder, and wherein the first and the second beam paths extend through the objective arrangement, and a retaining apparatus, on which the optics unit is mounted, the optics unit rotatable about a first axis of rotation, the first axis of rotation at least approximately corresponding to an axis of the objective arrangement, wherein the retaining apparatus comprises a retaining bracket, the retaining bracket engages over a housing that includes the optics unit, the optics unit being mounted to the housing and rotatable about the first axis of rotation, and wherein the optical observation instrument has a viewing direction that is angled in relation to the axis of the objective arrangement and comprises a deflection element, arranged on an object-side of the objective arrangement, and configured to deflect the first and the second beam paths into the objective arrangement, setting a viewing direction to the object field, setting an alignment of a stereo basis by rotating the optics unit about the first axis of rotation, recording stereo half images by the at least one electronic image recorder of the optical observation instrument, and displaying the stereo half images on a display device.

* * * * *

UNITED STATES PATENT AND TRADEMARK OFFICE
CERTIFICATE OF CORRECTION

| | |
|---|---|
| PATENT NO. | : 11,953,669 B2 |
| APPLICATION NO. | : 17/145495 |
| DATED | : April 9, 2024 |
| INVENTOR(S) | : Jonas Forster et al. |

Page 1 of 1

It is certified that error appears in the above-identified patent and that said Letters Patent is hereby corrected as shown below:

In the Claims

• Column 21, Claim 1, Lines 38-45, please delete:
"a retaining apparatus, on which the optics unit is mounted, the optics unit rotatable about the objective arrangement, wherein the retaining apparatus comprises a retaining bracket, which a first axis of rotation, the first axis of rotation at least approximately corresponding to an axis of the objective arrangement, wherein the retaining apparatus comprises a retaining bracket, which engages over the optics units, which is arranged"

And insert:
-- a retaining apparatus, on which the optics unit is mounted, the optics unit rotatable about a first axis of rotation, the first axis of rotation at least approximately corresponding to an axis of the objective arrangement, wherein the retaining apparatus comprises a retaining bracket, which engages over the optics unit, which is arranged --, therefore.

Signed and Sealed this
Twenty-ninth Day of July, 2025

Coke Morgan Stewart
*Acting Director of the United States Patent and Trademark Office*